United States Patent [19]

Chang et al.

[11] 4,440,668

[45] Apr. 3, 1984

[54] CATALYST FOR THE CONVERSION OF SYNTHESIS GAS TO HIGHER ALCOHOLS

[75] Inventors: Clarence D. Chang, Princeton; Patrick D. Perkins, Titusville, both of N.J.

[73] Assignee: Mobil Oil Corporation, New York, N.Y.

[21] Appl. No.: 395,403

[22] Filed: Jul. 6, 1982

[51] Int. Cl.$^3$ .................... B01J 21/06; B01J 23/72; B01J 23/78
[52] U.S. Cl. .................................... 502/331; 518/713
[58] Field of Search ............... 252/469, 471, 474; 518/713

[56] References Cited

U.S. PATENT DOCUMENTS

| | | | |
|---|---|---|---|
| 2,061,470 | 11/1936 | Larson | 518/713 |
| 4,081,510 | 3/1978 | Kato et al. | 252/469 X |
| 4,122,110 | 10/1978 | Sugier et al. | 252/464 X |
| 4,153,581 | 5/1979 | Habermann | 252/474 X |

FOREIGN PATENT DOCUMENTS 644526  1/1979  U.S.S.R. ................ 252/469

*Primary Examiner*—W. J. Shine
*Attorney, Agent, or Firm*—Alexander J. McKillop; Michael G. Gilman; Richard D. Stone

[57] ABSTRACT

Synthesis gas is converted with high selectivity to higher alcohols over a three component oxide catalyst based on
 (i) copper
 (ii) a metal of Group VIA, VIIA or VIIIA
 (iii) a metal of Group IVA or VA.

The preferred catalyst is based on copper, cobalt and zirconium with the first two components being formed by co-precipitation in the presence of the oxide third component.

3 Claims, No Drawings

CATALYST FOR THE CONVERSION OF SYNTHESIS GAS TO HIGHER ALCOHOLS

BACKGROUND OF THE INVENTION

This invention relates to the conversion of synthesis gas to alcohols with a selectivity towards the production of higher alcohols.

THE PRIOR ART

Methanol has been produced commercially for a long time by synthesis from pressurized mixtures of hydrogen, carbon monoxide and carbon dioxide gases in the presence of heterogeneous metallic catalysts. The initial high pressure processes using zinc oxide-chromium oxide catalyst were later replaced by medium and low pressure processes employing copper oxide-zinc oxide catalysts even though these catalysts were sufficiently sensitive to poisons as to require careful purification of the feed streams. The catalyst may be supported on metallic copper in order to prevent local overheating in the catalyst bed.

The use of aluminum oxide as an additional component for the copper oxide-zinc oxide catalysts has been known for some time being described, for example in "Synthesis of Methanol from Carbon Monoxide and Hydrogen", Industrial and Engineering Chemistry 20 (1928), 285–290. U.S. Pat. No. 4,111,847 also describes the use of alumina and other materials such as zirconia, titania, silica, calcia or magnesia as thermal stabilizers for copper oxide-zinc oxide catalysts. British Pat. No. 1,159,035 describes similar catalyst systems based on the oxides of copper and zinc together with alumina, titania, zirconia, ceria or thoria, optionally with the addition of chromia. Catalyst systems of this kind are said to be capable of operation for long periods of time at low pressures and temperatures, while producing only small amounts of organic impurities. U.S. Pat. No. 3,790,505 also describes catalysts of this kind.

Chromium oxide has also been proposed for use in combination with zinc oxide and copper oxide low temperature methanol synthesis of the kind disclosed in U.S. Pat. No. 3,326,956, even though the catalysts of this kind have poor resistance to aging and are relatively sensitive to poisons, as described in the article by Natta in Catalysis, Vol. III, Emmett, Reinhold 1955, and in DE-AS No. 1300538. Chromia is also proposed as a substitute for alumina in copper oxide-zinc oxide based system in U.S. Pat. No. 3,850,850.

A four component catalyst for synthesizing alcohols from synthesis gas is proposed in U.S. Pat. No. 4,122,110; the catalyst comprises components derived from copper, cobalt, a third metal (Cr, Fe, V or Mn) and an alkali metal, preferably lithium, sodium or potassium. Other components may also be present e.g. a zinc component. The selectivity of this catalyst to the production of alcohols is said to be high with practically no hydrocarbons being produced.

SUMMARY OF THE INVENTION

It has now been found that synthesis gas may be converted to mixtures of alcohols over catalyst systems which exhibit a selectivity towards the production of higher alcohols. The higher alcohols may be used as such as gasoline additives or they may be used industrially, for example, by conversion to hydrocarbons or to olefins which themselves may be converted to higher aliphatic hydrocarbons or aromatics.

The catalyst system according to the present invention consists essentially of three components derived from the following metals:
1. Copper
2. A metal of Group VIA, VIIA or VIIIA
3. A metal of Group IVA or VA (The Periodic Table used in this specification is the table approved by IUPAC and the U.S. National Bureau of Standards shown, for example in the Periodic Chart of the Fisher Scientific Company, Catalog No. 5-702-10).

The catalyst is preferably prepared by co-precipitation of the components from their aqueous solutions, suitably with an alkali metal carbonate, after which the co-precipitated components may be calcined to form what is believed to be a perovskite ($ABO_3$) structure containing the copper component as an additional constituent.

DESCRIPTION OF PREFERRED EMBODIMENTS

The present catalysts have three essential components which are derived, respectively, from the following metals:
1. Copper
2. A metal of Groups VIA, VIIA or VIIIA
3. A metal of Groups IVA or VA The second component is preferably derived from a base metal of Group VIIIA such as iron, cobalt or nickel, with cobalt and nickel being preferred but the other metals of the specified Groups namely, chromium, molybdenum, tungsten or manganese may also be employed. The third component is preferably derived from zirconium but titanium or vanadium are other suitable metals.

The ratio of the components is generally selected so that the second and third components are present in approximately equiatomic proportions, based on the metal. These compounds, when in their oxide forms in the catalyst, are believed to combine to form a perovskite structure which serves to retain the copper component and prevent its migration during synthesis conditions. However, since the activity of the catalyst may be retained over a range of component ratios, the individual components may be present in varying proportions which are normally within the ranges specified below in Table 1.

TABLE 1

| Catalyst Component, Atomic Proportions | | |
|---|---|---|
| | Broad | Preferred |
| 1. Copper | 1–50 | 1–4 |
| 2. Cr. etc. | 1–50 | 1–4 |
| 3. Zr. etc. | 1–50 | 1–4 |

The catalyst is preferably formed by co-precipitating the metals in the form of their carbonates from aqueous solutions of their compounds. It is preferred to use alkali metal carbonates, e.g. sodium carbonate or potassium carbonate as the precipitant since it has been found that minor amounts of alkali promote the desired reactions. Other carbonates e.g. ammonium carbonate may be used if desired. It is not essential that all the components should be co-precipitated and, in fact, it is often more convenient to precipitate the copper component and the third component (Co, Ni, etc.) from a solution which contains the second component suspended in it e.g. in the form of zirconia (ZrO$_2$) or titania (TiO$_2$). As another alternative, the catalyst components may simply be admixed e.g. by ball milling, high shear mixing or even by simple mixing.

If a precipitation procedure is used, the solution should, for preference, be at an elevated temperature e.g. 80° C. to 90° C. in order to ensure a finely-textured precipitate. Precipitation is normally completed within a few minutes but the mixture may be stirred for a few hours to ensure complete recovery of the catalyst components from the solution. The pH of the solution should normally be brought to a slightly alkaline value in order to ensure complete precipitation but care should be taken to avoid excessively alkaline conditions especially when ammonium carbonate is used as the precipitant since there is then a risk of soluble complex species being formed. With ammonium carbonate as the precipitant, the pH of the solution should be adjusted to 6.8±0.1.

After the precipitation or mixing steps have been completed, the powdered catalyst may be washed after which calcination is carried out, suitable at a temperature of 300° C. to 600° C. and usually in the range of 350° C. to 450° C. During the calcination, carbonates will generally be converted to oxides and it is believed that a perovskite (ABO$_3$) structure may be formed by the second and third components and that this will serve to prevent migration of the copper component in use. The catalyst may be pelletized either before or after calcination although for practical reasons, pelletising prior to calcination will be preferred.

The calcined catalyst is preferably subjected to a preliminary reduction treatment in hydrogen or hydrogen diluted with syngas or an inert gas such as nitrogen or helium. Suitable temperatures for this preliminary treatment step are from 100° C. to 400° C. and normally the temperature will be raised progressively over a period of about 6 to 48 hours in order to ensure satisfactory activation of the catalyst.

A minor amount of an alkali metal compound may be added to the catalyst since it has been found that this will promote the formation of the desired higher alcohols. The alkali metal may be used in the form of the hydroxide or a salt and may suitable be incorporated into the catalyst by impregnation with a solution of the compound. In general, from 1 to 20 weight percent alkali metal, preferably 2 to 10 weight percent, calculated as the metal and based on the total weight of catalyst will be sufficient.

The present catalysts are notable for their selectivity towards the production of higher alcohols from synthesis gas; only small amounts of hydrocarbons and other products are obtained. Although methanol is obtained in the synthesis, the proportion of the higher alkanols are higher than with other catalysts.

Synthesis conditions, apart from the identity of the catalyst, will generally be the same as with conventional methanol synthesis processes. For example, reaction temperatures will normally be in the range of 150° C. to 400° C., preferably 200° C. to 300° C. with pressures typically being at least 2000 kPa and more commonly from 5000 to 20000 kPa. High space velocities are usually employed e.g. 1000 to 20000 GHSV.

The synthesis gas is preferably a gas with a relatively low ratio of hydrogen to carbon monoxide since high hydrogen ratios do tend to favor the production of methane. In general, the molar ratio of H$_2$:CO will be from about 0.4:1 to 10:1 with ratios from 0.4:1 to 3:1 being preferred. Low ratio synthesis gas (H$_2$:CO less than 1:1) is economically produced by modern high efficiency gasifiers and if higher hydrogen ratios are desired, any deficiency may be remedied by making use of the water gas shift by injecting steam into the feed or into the catalyst. Alternatively, the steam may be added to the synthesis gas and the mixture passed over a separate water gas shift catalyst. The synthesis gas itself may be obtained from a suitable gasifier, as is conventional.

The catalyst may be oxidatively regenerated, suitably by heating in an oxidizing atmosphere at temperatures from 200° to 500° C., although the lower temperatures within this range will be preferred for extended regenerations.

The invention is illustrated by the following Example in which all parts, proportions and percentages are by weight unless the contrary is stated.

EXAMPLE

Zirconia, ZrO$_2$ (25 g.) prepared by the hydrolysis of ZrCl$_4$ followed by washing and calcination at 300° C. was added to a solution of Cu(NO$_3$)$_2$.nH$_2$O (23.15 g.) and Co(NO$_3$)$_2$.6H$_2$O (29.10 g.) in 200 ml. water. After precipitation of the metal components at 80° C.-90° C. by the addition of 1 M K$_2$CO$_3$ solution, the material was filtered, dried at 110° C. and calcined for 2 hours at 400° C. The calcined catalyst was then impregnated with 5% potassium as KOH and calcined again at 400° C. for 2 hours.

After a preliminary reduction treatment by heating from 100° C. to 205° C. over 20 hours in an atmosphere of 8.5% hydrogen in helium, the catalyst was used in the synthesis of alcohols. A 50:50 volume percent mixture of hydrogen and carbon monoxide was passed over the catalyst at 250° C., 6300 kPa, 4000 GHSV to produce the organic products shown in Table 2 below.

TABLE 2

| Synthesis Products | |
| --- | --- |
| Product | Wt. Percent |
| Alcohols | 81.9 |
| Paraffins | 8.9 |
| Esters | 4.9 |
| Aldehydes | 4.3 |

The distribution of the alcohols is shown in Table 3 below.

TABLE 3

| | Alcohol Distribution |
| --- | --- |
| C$_1$ | 34.7 |
| C$_2$ | 27.2 |
| C$_3$ | 13.3 |
| C$_4$ | 10.8 |
| C$_5$+ | 14.0 |

We claim:
1. A catalyst for the production of alcohols from synthesis gas which consists essentially of the oxides of
   (i) copper
   (ii) cobalt
   (iii) zirconium and
   (iv) an alkali metal.
2. A catalyst comprising oxides of:
   (i) copper
   (ii) cobalt
   (iii) zirconium and
   (iv) an alkali metal characterized by its method of preparation, said method comprising co-precipitating compounds of said copper, cobalt and zirconium components from aqueous solutions thereof at co-precipitation conditions, calcining said precipitant to convert the metals to their oxide forms, impregnating said calcined precipitant with an aqueous solution of a compound of said alkali metal and calcining to form the alkali metal oxide.

3. Catalyst of claim 1 characterized by co-precipitation of said copper, cobalt and zirconium as carbonates at a temperature of 80° to 90° C. using potassium carbonate as a precipitant, in a solution maintained at a pH of 6.7 to 6.9.

* * * * *